US006330336B1

(12) United States Patent
Kasama

(10) Patent No.: US 6,330,336 B1
(45) Date of Patent: Dec. 11, 2001

(54) ACTIVE SILENCER

(75) Inventor: Minoru Kasama, Nakai-machi (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 08/986,193

(22) Filed: Dec. 5, 1997

(30) Foreign Application Priority Data

Dec. 10, 1996 (JP) .................................................. 8-329286

(51) Int. Cl.[7] .......................... A61F 11/06; G10K 11/16; H03B 29/00

(52) U.S. Cl. ...................... 381/71.1; 381/71.5; 381/71.8; 381/71.11

(58) Field of Search ............................... 381/71.7, 71.11, 381/71.14, 71.8, 71.1, 71.2, 71.3, 71.5, 71.12, 94.01, 94.9

(56) References Cited

U.S. PATENT DOCUMENTS 5,105,377 * 4/1992 Ziegler, Jr. ........................ 381/71.11
5,377,276 * 12/1994 Terai et al. ........................ 381/71.11
5,388,080 * 2/1995 Feintuch et al. .
5,481,615 * 1/1996 Eatwell et al. .................... 381/71.11
5,544,201 * 8/1996 Hoshino et al. ..................... 375/350
5,652,799 * 7/1997 Ross et al. ........................ 381/71.11
5,832,095 * 11/1998 Daniels .............................. 381/71.5

FOREIGN PATENT DOCUMENTS

A-57-97989 6/1982 (JP) .
A-59-9699 1/1984 (JP) .
A-2-103366 4/1990 (JP) .
A-2-97877 4/1990 (JP) .
A-3-263573 11/1991 (JP) .
A-4-221965 8/1992 (JP) .
A-4-221967 8/1992 (JP) .
A-4-332673 11/1992 (JP) .
A-6-8581 1/1994 (JP) .
406067681 * 3/1994 (JP) .

* cited by examiner

*Primary Examiner*—Duc Nguyen
(74) *Attorney, Agent, or Firm*—Oliff & Berridge, PLC

(57) ABSTRACT

Pseudo space transmitting signal processing means of the signal processing means simulates the frequency response of the space up to the silencing point from a noise source, while pseudo inverse filter signal processing means simulates an inverse filter characteristic 1/(K×Sp×G1) for canceling the characteristic of the combined frequency response (K×Sp×G1) of K of noise input means, Sp of a secondary sound source speaker, and G1 up to a silencing point from a secondary sound source speaker. The pseudo space transmitting signal processing means and pseudo inverse filter signal processing means set a gain characteristic equal to an original space transmitting characteristic and inverse filter characteristic, respectively. Moreover, the pseudo space transmitting signal processing means is structured to provide a delay of phase for an amplitude characteristic, while the pseudo space transmitting signal processing means is structured to lead the phase as much as a delay of the pseudo inverse filter signal processing means. Thereby, the present invention can provide an active silencer comprising signal processing means for generating signal for canceling noise and having a stable filter characteristic.

7 Claims, 14 Drawing Sheets

ACTIVE SILENCER

BACKGROUND OF THE INVENTION

1. Field of the Invention

The present invention relates to an active silencer and particularly to an active silencer which utilizes the technique for canceling noise by generating the sound having the waveform in the same amplitude but inverse phase from the noise generated from a noise source and then causing these sounds to interfere with each other.

2. Description of the Related Art

As the technique for generating a secondary sound in the same amplitude and inverse phase from noise to cancel these sound by causing these noise and secondary sound to interfere with each other, there are examples described in the Official Gazettes, Japanese Published Unexamined Patent Application Nos. Hei 4-221965 and Hei 4-221967.

FIG. 15 is a diagram showing an example of a basic structure of a silencer of the related art. In FIG. 15, a noise source 1 is surrounded by a duct 2 in its peripheral space. However, the cross-sectional shape of the duct 2 must be within the range in which the sound wave radiated from the noise source 1 can be assumed as a plane wave. An input microphone 3 is provided in the vicinity of the noise source 1 to detect noise from the noise source. An output of the input microphone 3 is input to signal processing means 4 and its output is then connected to a secondary sound source speaker 5. In this figure, K indicates the frequency response characteristic of the input microphone 3, while G0 indicates the frequency response characteristic of the area up to the silencing point 6 from the noise source 1, G1 indicates the frequency response characteristic of the area up to the silencing point 6 from the secondary sound source speaker 5, Sp indicates the frequency response characteristic of the secondary sound source speaker 5 and C indicates the frequency response characteristic of signal processing means 4.

Noise radiated from the noise source 1 reaches the silencing point 6 passing through the inside of duct 2. Meanwhile, a signal detected by the input microphone 3 is input to signal processing means 4, it is then processed as explained later and output as the secondary sound controlled from the secondary sound source speaker 5 and reaches the silencing point 6. At the silencing point 6, noise waveform of the noise source 1 and the secondary sound from the secondary sound source speaker 5 interfere with each other and thereby sound pressure becomes zero. The duct 2 is provided to approximate the sound wave in the duct to the plane wave propagated in the longitudinal direction of duct and the fact that the sound pressure in the silencing point 6 becomes zero is thought to suggest that the sound pressure at the cross-section including the silencing point 6 and in the space in the downstream side thereof is also zero.

Here, the signal processing method in the signal processing means 4 will be explained. First, the frequency response characteristic of the area up to the silencing point 6 from the noise source 1 including the secondary sound source speaker 5 and signal processing means 4 is expressed by the following formula.

$$G0+K\times C\times Sp\times G1 \quad (1)$$

Therefore, following condition is required to perfectly reduce the noise of the noise source 1 at the silencing point 6.

$$G0+K\times C\times Sp\times G1=0 \quad (2)$$

From this formula, $$C=-G0\times 1/(K\times Sp\times G1) \quad (3)$$

Therefore, the signal processing means 4 may be structured depending on each frequency response characteristic. Since the frequency response characteristic to form the signal processing means 4 is fixed, this system is hereinafter called as the fixed parameter system.

Moreover, the Official Gazettes, Japanese Published Unexamined Patent Application Nos. Hei 4-332676 and Hei 6-8581 describe a system wherein the secondary sound is combined using the method of applied algorithm. A structure of the basic system is shown in FIG. 16.

FIG. 16 shows an example of another basic structure of the silencer of the related art. In FIG. 16, a noise source 1 is surrounded by a duct 2, a detection microphone 7 is provided in the vicinity of the noise source 1 and an error detection microphone 8 is also provided at the downstream side of the duct 2. Outputs of these detection microphone 7 and error detection microphone 8 are input to signal processing means 9 and an output of this signal processing means 9 is connected to a secondary sound source speaker 5. The signal processing means 9 is provided with an application filter 9*a*.

The application filter 9*a* updates the coefficients depending on the following formula on the basis of the noise signal x(t) caught by the detection microphone 7 and an error signal e(t) caught by the error detection microphone 8.

$$H(i)_{new}=h(i)_{old}+k\times e(t)\times x(t-1) \quad (4)$$

Where, h(i)(i=0 . . . , n) is a coefficient of the application filter 9*a*, n is the maximum order number of the application filter 9*a*, x(t−1) is a preceding noise signal, and k is a constant. The signal processed by the application filter 9*a* of which coefficient is updated is sent to the secondary sound source speaker 5 and is then radiated as the sound wave.

This algorithm is called the Filtered-X algorithm and when this applicable operation is repeated, the error signal e(t) comes close to zero to realize silencing.

In this system, it is not required to previously obtain each frequency response expressed by the formula (3) in the fixed parameter system and moreover this system has a merit that variation in the frequency response due to the environmental change can also be covered. This system is hereinafter called as the application parameter system for the convenience of the explanation.

As the other examples of the application parameter system, there are official gazettes of the Japanese Published Unexamined Patent Application Nos. Hei 2-97877 applied to a compressor noise of a home electric refrigerator, Sho 59-9699 applied to control of sound field within chamber of automobile and Sho 7-97989 applied to the duct of air conditioner. In any of these examples, the structure same as that of FIG. 16 has been employed.

In the fixed parameter system described in the Official Gazette of Japanese Published Unexamined Patent Application No. Hei 4-221965, the characteristic 1/(K×Sp×G1) of the formula (3) called generally as the inverse filter is realized to cancel (K×Sp×G1), however, under the condition that the initial characteristic (K×Sp×G1) must be the minimum phase system which does not results in any delay of phase for the gain characteristic.

However, in general, many acoustic transfer systems surely allow existence of time delay until the sound wave reaches the output point from the input point. Therefore, the condition of the minimum phase system is not satisfied.

Accordingly, when the signal processing means is formed depending on the formula (3) from the measured each frequency response, it operates as an unstable filter which disperses an output to an finite input. Moreover, when non-minimum phase is forcibly approximated by the minimum phase, the signal processing means will change to signal processing means under the causal relationship in which a future information which is leading as much as an amount of delay for the current input is previously required to compensate for the amount of delay. However, such signal processing means cannot be realized easily.

However, in the examples described in the Official Gazettes of the Japanese Published Unexamined Patent Application Nos. Hei 4-221965 and Hei 4-221967 explained previously, it is described that silencing can be realized only by introducing the formula (3), and such problem is not yet explained.

Meanwhile, in the application parameter system described in the Official Gazettes of the Japanese Published Unexamined Patent Application Nos. Hei 4-332673 and Hei 6-8581, a filter having the characteristic similar to that of the formula (3) is approximated using the application arithmetic operation and is formed by FIR (Finite Impulse Response) filter assuring its stability. Therefore, stability and causal relationship of the application filter itself can be assured.

However, the FIR filter assures stability while it has a property to require a considerable time for calculation. Moreover, it is always accompanied by the limitation that all processes such as detection of noise, applicable arithmetic operation, arithmetic operation for the sound in the inverse waveform from that of noise, and generation of inverse waveform sound must be completed within the time until the sound generated by the noise source reaches the secondary sound source speaker which generates the sound of inverse waveform. Therefore, in view of providing the calculation time, the distance between the noise source and secondary sound source speaker must be isolated to a certain degree. As a result, a silencer must become large in size and it is difficult to reduce the size thereof.

In addition, as is described in the Official Gazettes of the Japanese Published Unexamined Patent Application Nos. Hei 2-103366 and Hei 3-263573, an application control system has a property that the system as a whole becomes unstable easily in some cases if a sudden disturbance such as the calling sound of a telephone call generated in an office is detected by a microphone for measuring noise or an error detection microphone for detecting the silencing result. In such a case, there is a risk that the sound which is higher than the noise source to be silenced is radiated from the secondary sound source speaker.

Moreover, in order to maintain high speed arithmetic operation in the application control, it is requested to introduce an exclusive and expensive DSP (Digital Signal Processor) circuit into the signal processing means. But it has been a cause of increase in cost of the silencer.

OBJECT AND SUMMARY OF THE INVENTION

Considering the background explained previously, the present invention has been proposed to provide an active silencer in which signal processing means for generating a signal to cancel the noise has been formed with a stable filter circuit.

In order to solve the problems explained above, the present invention provides an active silencer which comprises noise input means to obtain a noise signal from noise generated from a noise source, signal processing means to convert the noise signal obtained from the noise input means into the signal of the waveform in the same amplitude and inverse phase from the noise waveform transmitted from the noise source and a secondary sound source speaker to radiate the signal converted by the signal processing means as the sound wave for interference between the noise sound from the noise source and the sound wave radiated from the secondary sound source speaker at the preset silencing point, whereby the signal processing means comprises pseudo space transmitting signal processing means for converting the noise signal obtained from the noise input means into the signal having the same amplitude characteristic as the frequency response characteristic of the sound wave up to the silencing point from the noise source and also having the phase characteristic which is led by the predetermined amount for such frequency response characteristic and pseudo inverse filter signal processing means for converting, through the noise input means, the secondary sound source speaker, and the space from the secondary sound source speaker to the silencing point, the signal converted by the pseudo space transmitting signal processing means into the signal having the amplitude characteristic inverted from the frequency response characteristic up to the silencing point and also having the phase characteristic which is delayed by the predetermined amount from the inverted positive or negative phase for such frequency response characteristic.

According to such active silencer, the pseudo space transmitting signal processing means has the original space transmitting characteristic for the gain characteristic and the pseudo inverse filter signal processing means also has the inverse filter characteristic in the gain characteristic. However, in regard to the phase characteristic, when a model of the pseudo inverse filter signal processing means is accurately formed in which the original combined frequency response characteristic is inverted positively or negatively, such model becomes unstable and therefore the phase characteristic of the pseudo inverse filter signal processing means is delayed for the predetermined amount. Thereby, unstable operation of the filter may be avoided. Meanwhile, amount of phase delayed by the pseudo inverse filter signal processing means is led by the pseudo space transmitting signal processing means. Thereby, amount of phase manipulated for stabilization of the filter can be canceled when the signal has passed the pseudo space transmitting signal processing means and pseudo inverse filter signal processing means. The sound wave in the same amplitude and inverse phase from the sound wave from the noise source can be obtained at the silencing point by multiplying −1 to the signal obtained from the couple of signal processing means and then radiating such signal as the sound wave from the secondary sound source speaker.

The present invention also stabilizes the filter by equalizing the phase characteristic of the pseudo inverse filter signal processing means to the minimum phase characteristic calculated from the gain characteristic of the signal processing means.

In this case, the silencing point is set far from the position of the secondary sound source speaker when the noise input means is defined as the base point, the predetermined amount for leading the phase characteristic in the pseudo space transmitting signal processing means is equal to the time for delaying the phase characteristic in the pseudo inverse filter signal processing means, and the predetermined amount for delaying the phase characteristic in the pseudo inverse filter signal processing means is determined depending on the phase difference between the minimum phase of the frequency response characteristic up to the silencing point and actual phase through the noise input means, secondary sound source speaker, and the space between the secondary sound source speaker and the silencing point.

Otherwise, the silencing point is set far from the position of the secondary sound source speaker when the noise input means is defined as the base point, the predetermined amount for leading the phase characteristic in the pseudo space transmitting signal processing means is determined depending on the phase difference between the minimum phase of the frequency response characteristic of the sound wave up to the silencing point from the noise source and the actual phase, and the predetermined amount for delaying the phase characteristic in the pseudo inverse filter signal processing means is determined depending on the phase difference between the minimum phase of the frequency response characteristic up to the silencing point and the actual phase through the noise input means, secondary sound source speaker, and the space between the secondary sound source speaker and the silencing point.

The present invention further comprises measuring means for measuring the frequency response up to the silencing point from the noise source, frequency response of the noise input means, frequency response of the secondary sound source speaker, and frequency response up to the silencing point from the secondary sound source speaker and retrial setting means for updating, in every predetermined time, the frequency response of the pseudo space transmitting signal processing means and pseudo inverse filter signal processing means depending on the result of measurement by the measuring means.

As explained previously, the frequency response of each part to constitute the pseudo space transmitting signal processing means, and pseudo inverse filter signal processing means is measured again in every predetermined time, and the pseudo space transmitting signal processing means and pseudo inverse filter signal processing means are re-structured depending on the result of measurement in accordance with the environmental change of the active silencer.

Moreover, the present invention further comprises silence detecting means for detecting the combined sound of the noise at the silencing point from the noise source and the sound wave from the secondary sound source speaker, silence effect monitoring means for comparing the combined sound detected by the silence detecting means and the preset allowable value, measuring means for measuring, when the combined sound compared by the silence effect monitoring means has exceeded the allowable value, frequency response up to the silencing point from the noise source, frequency response of the noise detecting means, frequency response of the secondary sound source speaker, and frequency response up to the silencing point from the secondary sound source speaker, and changing means for changing frequency response characteristic of the pseudo space transmitting signal processing means and the pseudo inverse filter signal processing means depending on the result of measurement by the measuring means.

Accordingly, if the signal detected at the silencing point by the silence detecting means has exceeded the preset allowable value, a certain frequency response characteristic is judged to be changes as much as it cannot be neglected due to the aging, and the frequency response of each part forming the pseudo space transmitting signal processing means and pseudo inverse filter signal processing means is measured again by the measuring means, and such pseudo space transmitting signal processing means and pseudo inverse filter signal processing means are re-structured depending on such result in accordance with the environmental change of the active silencer.

Moreover, according to the present invention, there is provided an active silencer comprising noise input means for obtaining a noise signal from noise generated from a noise source, signal processing means for converting the noise signal obtained from the noise input means into the signal in the same amplitude and inverse phase from the noise waveform transmitted from the noise source and fixing the input/output transmission characteristic for the time during control of silence, and a secondary sound source speaker for radiating an output signal of the signal processing means as the sound wave, whereby interference is generated between the noise from the noise source and the sound wave from the secondary sound source speaker at the preset silencing point.

According to such active silencer, the frequency response characteristic of the signal processing means for combining the secondary sound in the same amplitude and inverse waveform from the noise waveform of the noise signal detected is presumed or designed. Thereby, since the application arithmetic operation which requires a considerable time is not carried out during the silence control, the calculation time can be reduced remarkably.

BRIEF DESCRIPTION OF THE DRAWINGS

Other objects and advantages of the present invention will be apparent from the following detailed description of the presently preferred embodiments thereof, which description should be considered in conjunction with the accompanying drawings in which.

DETAILED DESCRIPTION OF THE INVENTION

The preferred embodiments of the present invention will be explained with reference to the accompanying drawings.

Figure 1:
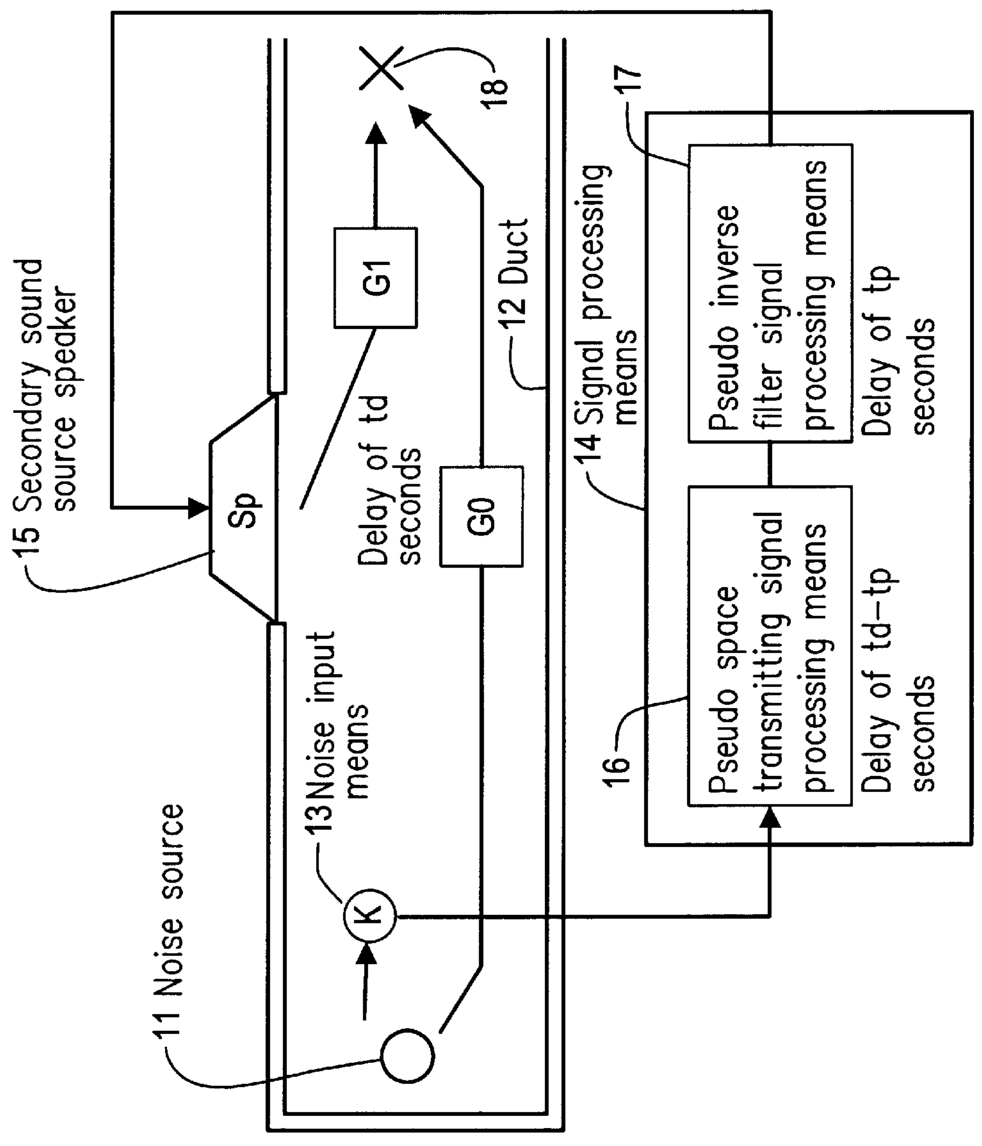
FIG. 1 is a diagram showing a principle structure of the present invention.

FIG. 1 is a diagram showing the principle structure of the present invention. An active silencer of the present invention comprises noise input means 13 which is provided in the vicinity of a noise source 11 in the duct 12 surrounding the noise source 11 to detect noise from the noise source 11, signal processing means 14 which receives an output of this noise input means 13 to convert into the signal waveform in the same amplitude and inverse phase from the noise waveform transmitted in the duct 12 from the noise source 11, and a secondary sound source speaker 15 which is connected to an output of the signal processing means 14 to radiate the secondary sound into the duct 12. The signal processing means 14 is composed of pseudo space transmitting signal processing means 16 and pseudo inverse filter signal processing means 17.

Here, in the signal processing means 14 for combining the secondary sound, from the noise waveform, in the same amplitude and inverse waveform therefrom, the pseudo space transmitting processing means 16 simulates the frequency response G0 of the noise propagated within the duct 12 up to the preset silencing point 18 from the noise source 11, while the pseudo inverse filter signal processing means 17 simulates the inverse filter characteristic 1/(K×Sp×G1) which cancels the combined frequency response (K×Sp×G1) characteristic of the frequency response K of the noise input means 13, frequency response Sp of the secondary sound source speaker 15, and frequency response G1 up to the silencing point 18 from the secondary sound source speaker 15.

However, the pseudo space transmitting signal processing means 16 and pseudo inverse filter signal processing means 17 are same as the original space transmitting characteristic and inverse filter characteristic in the gain characteristic but are respectively adjusted in the phase characteristic. Namely, when an accurate model of the pseudo inverse filter signal processing means 17 is formed by positively or negatively inverting the phase characteristic of the original combined frequency response, such model becomes unstable in operation. Therefore, in view of obtaining stable operation thereof, it is structured to have the minimum phase characteristic for the amplitude characteristic by manipulating the phase information. The pseudo inverse filter signal processing means 17 thus structured has a delay of tp seconds from the actual inverse filter characteristic 1/(K×Sp×G1). Moreover, since the frequency response G0 of the pseudo space up to the silencing point 18 from the noise source 11 is delayed by td seconds, the pseudo space transmitting signal processing means 16, although it has the intrinsic delay of phase as td seconds, leads the phase for tp seconds to provide the delay of phase of (td−tp) seconds. Thereby, the amount of phase manipulated by the pseudo inverse filter signal processing means 17 for stabilization of filter is compensated by the amount of phase led by the pseudo space transmitting signal processing means 16. After all, total amount of phase manipulation through the pseudo space transmitting signal processing means 16 and pseudo inverse filter signal processing means 17 may be canceled. The sound wave in the same amplitude and inverse phase from the sound wave transmitted from the noise source can be obtained by multiplying (−1) to the signal obtained by two signal processing means and then radiating such signal as the sound wave from the secondary sound source speaker. Thereby, both sound waves are interfered and noise amplitude can be reduced.

Figure 2:
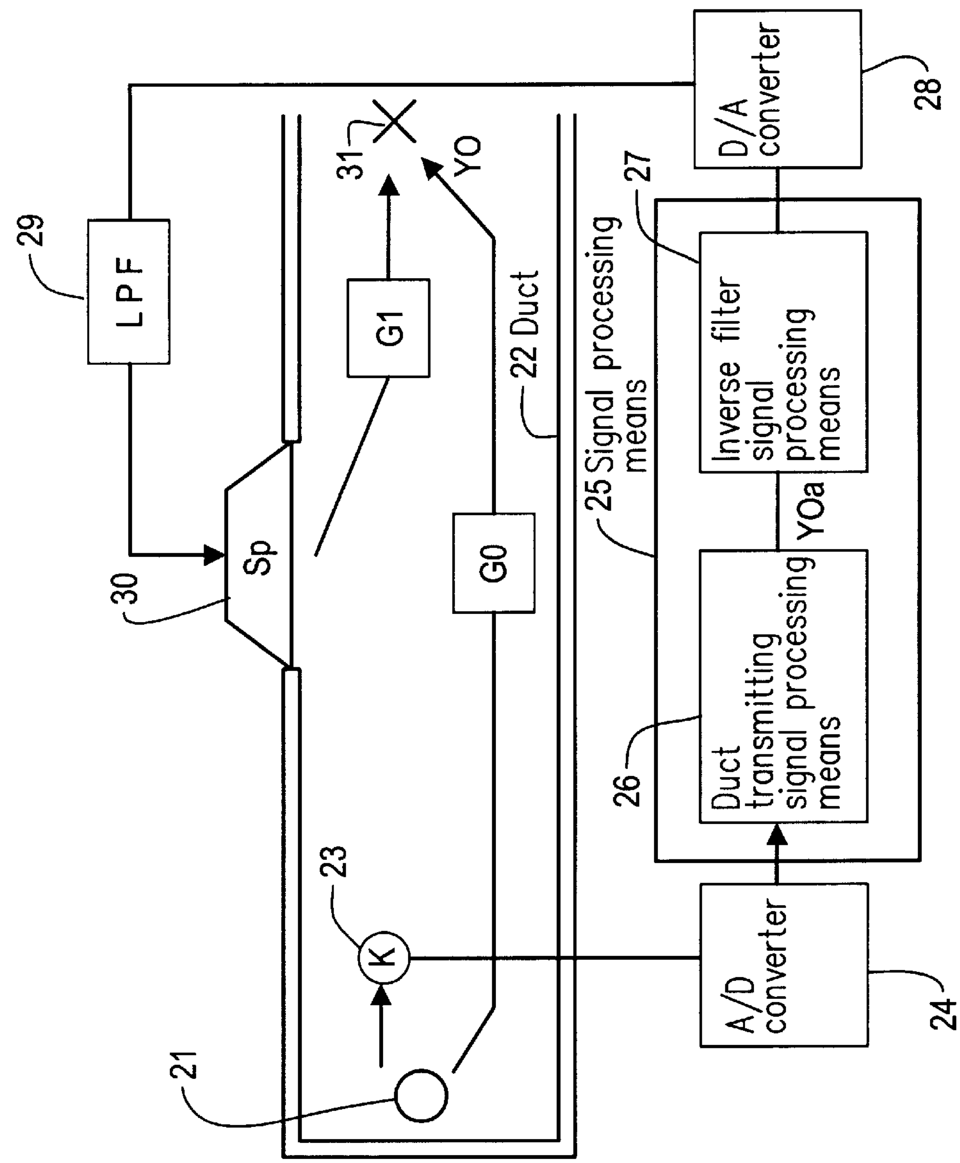
FIG. 2 is a diagram showing a preferred embodiment of an active silencer of the present invention.

FIG. 2 is a diagram showing a preferred embodiment of the active silencer of the present invention. According to FIG. 2, an input microphone 23 for detecting noise from a noise source 21 is provided in the vicinity of the noise source 21 within a duct 22 formed to surround the noise source 21. An output of the input microphone 23 is connected to an analog/digital (hereinafter referred to as A/D) converter 24 for converting an analog signal from this input microphone 23 into a digital signal. An output of the A/D converter 24 is connected to an input of signal processing means 25. This signal processing means 25 is composed of duct transmitting signal processing means 26 and inverse filter signal processing means 27. This inverse filter signal processing means 27 is capable of employing an IIR (Infinite Impulse Response) filter structure which assures high speed calculation rate. An output of the signal processing means 25 is connected to the secondary sound source speaker 30 via a digital/analog (hereinafter referred to as D/A) converter 28 and low-pass filter (LPF) 29.

The duct transmitting signal processing means 26 of the signal processing means 25 simulates frequency response characteristic up to the silencing point 31 from the noise source 21, while the inverse filter signal processing means 27 simulates the frequency characteristic for canceling the acoustic/electric conversion characteristic (K) when the noise signal is detected and the electric/acoustic characteristic (Sp, G1) when the signal is radiated after the silencing process.

The noise signal detected by the input microphone 23 is sent first to the duct transmitting signal processing means 26 of the signal processing means 25 via the A/D converter 24. The duct transmitting signal processing means 26 has not only the gain as the frequency response characteristic G0 up to the silencing point 31 from the noise source 21 but also the phase characteristic leading for the predetermined amount. Therefore, its output Y0*a* seems to be leading on the time axis when it is seen from the actual duct transmitting signal Y0.

Meanwhile, the inverse filter signal processing means 27 has the gain characteristic in the relation of inverse number in the gain characteristic to the combined frequency response (K×Sp×G1) of the frequency response K of input microphone 23, frequency response SP of secondary sound source speaker 30, and frequency response G1 up to the silencing point 31 from the secondary sound source speaker 30, namely the gain characteristic in the relation of 1/(K×Sp×G1). In regard to the phase, the inverse filter signal processing means 27 does not have the phase characteristic, in order to suppress appearance of unstable root, which is accurately inverted positively or negatively from the phase characteristic of the combined frequency response but the phase characteristic which is delayed by the predetermined amount therefrom.

Moreover, the digital signal processed by the signal processing means 25 is converted to an analog signal via the D/A converter 28. In this case, due to the principle factor of the D/A conversion, delay of phase which is proportional to the sampling frequency is generated.

Moreover, in order to reduce a high frequency element of the silencing signal in the high frequency range higher than the control object frequency, a low-pass filter 29 is required between the D/A converter 28 and the secondary sound source speaker 30, but delay of phase is also generated by this low-pass filter 29.

The phase in the area up to the silencing point 31 from the noise source 21 is virtually balanced by leading the phase delay up to the silencing point 31 from the inverse filter signal processing means 27 for the compensation in the duct transmitting signal processing means 26.

Figure 3:
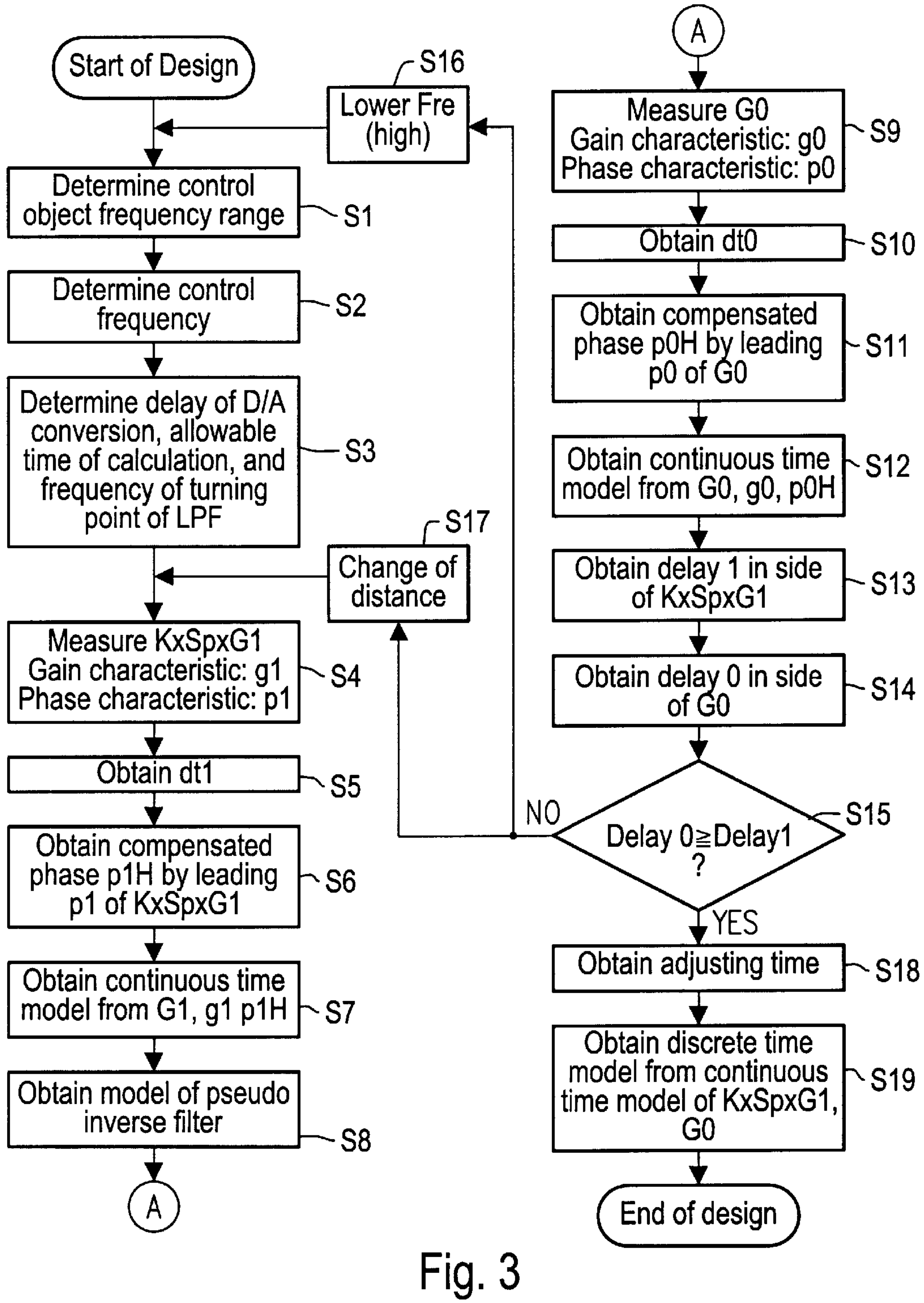
FIG. 3 is a flowchart showing the flow of design process for determination of frequency response characteristic of signal processing means.

The design flow chart for determination of the frequency response characteristic of the signal processing means 25 is shown in FIG. 3.

FIG. 3 is a flow chart showing the flow of design process for determination of frequency response characteristic in the signal processing means. First, frequency range of the control object is determined (Step S1). In regard to the range of the low frequency portion and high frequency portion to be silenced, the lower frequency limit Frq (low) and higher frequency limit Frq (high) are determined. Next, the control frequency is determined for the frequency range (Step S2). The control frequency is the sampling frequency in the digital processing and determines this frequency. Here, the control frequency Frq (control) is determined to 2.5 times the upper limit value of the frequency range. Namely, $$\text{Frq (control)}=2.5\times\text{Frq (high)} \tag{5}$$

Thereby, the values of D/A conversion delay, calculation allowance time, and the value of the frequency at the turning point of the low-pass filter are automatically determined (Step S3). Namely, when the control frequency Frq (control) is determined, since it is known that delay of the D/A conversion is theoretically equal to a half of the control frequency, delay of D/A conversion can be known first as expressed below.

$$\text{Delay of } D/A \text{ conversion}=1/(2\times\text{Frq (high)}) \tag{6}$$

Since the calculation allowance time indicates the calculation time in which the digital calculation process must be completed when the sampling is performed at the certain time, it can be obtained by the following formula.

$$\text{Calculation allowance time}=1/(\text{Frq(control)}) \tag{7}$$

In the high frequency portion exceeding the control object frequency range, a low-pass filter is provided to control the increase of gain of inverse filter. In this case, the frequency to rejecting the high frequency signal is determined as indicated below as the frequency at the turning point of the low-pass filter.

$$\text{Turning point frequency}=1/(2\times\text{Frq(control)}) \tag{8}$$

Next, the combined frequency response (K×Sp×G1) between the input microphone and silencing point is measured (Step S4). In this case, the gain characteristic is assumed as g1 and phase characteristic as p1. More specifically, a speaker is provided near the noise source to generate white noise therefrom. Such white noise is picked up by the input microphone and then it is radiated from the secondary sound source speaker via the signal processing means. The signals obtained from the input microphone and evaluation microphone provided at the silencing point are input, for example, to FET (high speed Fourier transform) analyzer to measure the combined frequency response up to the silencing point from the input microphone.

Next, the response delay dt1 between the secondary sound source speaker and the evaluation microphone provided at the silencing point is obtained (Step S5). This value may be obtained by the following formula.

$$dt\mathbf{1}=\text{Distance between the secondary sound source speaker and evaluation microphone/sound velocity} \tag{9}$$

The compensated phase p1H is obtained by leading the phase p1 of the combined frequency response (K×Sp×G1) (Step S6). It is intended to execute compensation by leading the phase for the pure delay of time in order to stable the inverse filter when it is made. The compensated phase p1H is expressed by the following formula.

$$p\mathbf{1}H=p\mathbf{1}+(D/A\text{ conversion delay}+dt\mathbf{1})\times 360\times\text{frequency} \tag{10}$$

Characteristic example of the combined frequency response (K×Sp×G1) compensated to eliminate time delay is shown in FIG. 4.

Figure 4A:
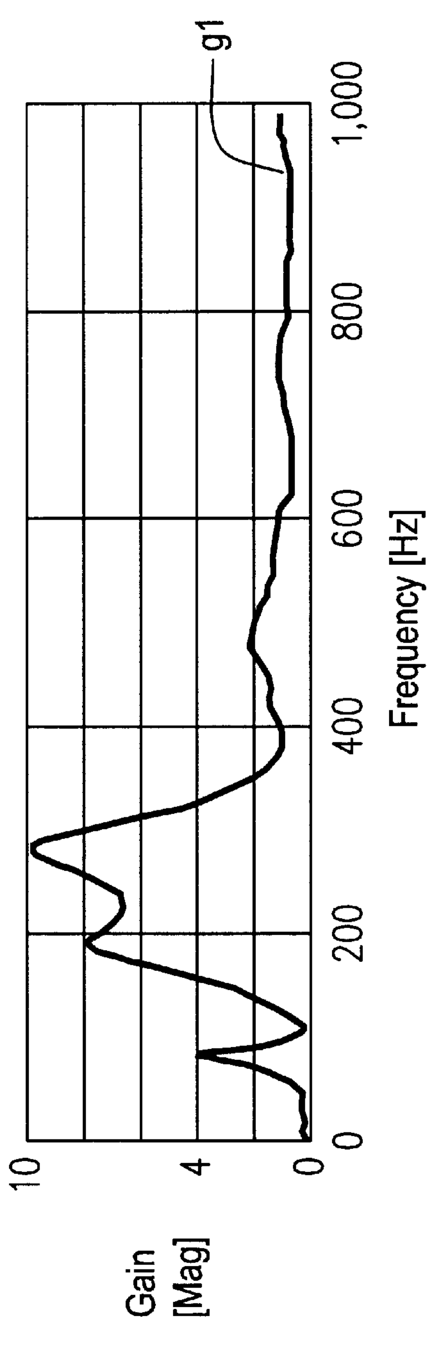
FIG. 4 shows an example of the compensated combined frequency response characteristic; (A) is the gain characteristic of the combined frequency response and (B) is the compensated phase characteristic.
Figure 4B:
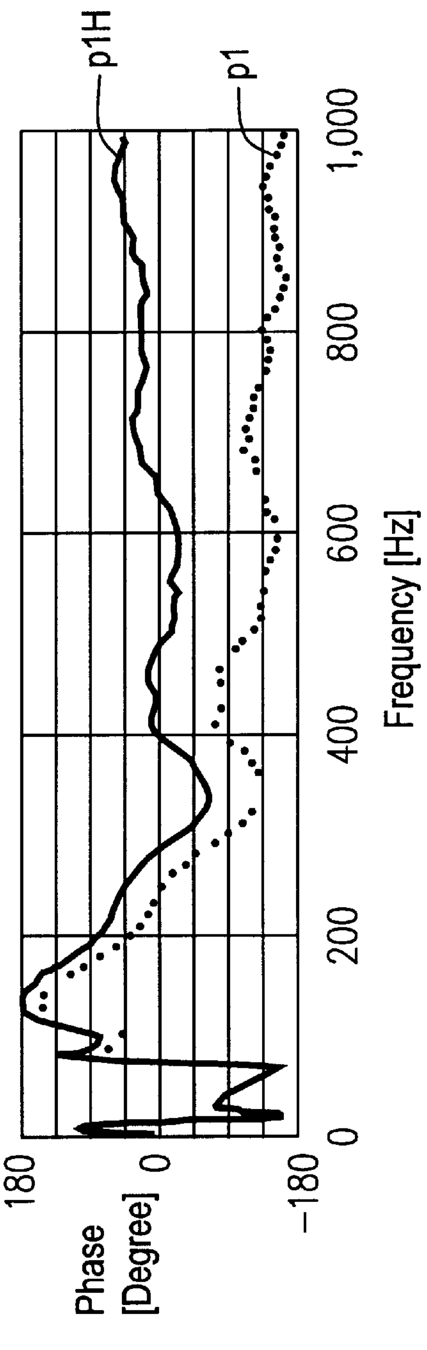

FIG. 4 is a diagram showing an example of the combined frequency response characteristic. FIG. 4(A) shows the gain characteristic of the combined frequency response and FIG. 4(B) shows the compensated phase characteristic. Here, the gain characteristic shown in FIG. 4(A) is the gain characteristic g1 measured in the step S4. In the phase characteristic shown in FIG. 4(B), a broken line indicates the original phase p1 measured in the step S4, while a solid line indicates the compensated phase p1H in which the phase is led to eliminate time delay depending on the formula (10).

Next, a continuous time model using a Laplace's operator s is obtained using the information of compensated phase characteristic p1H (Step S7). More specifically, it can be realized by curve fitting to the information of gain and phase. This curve fitting is a method to obtain the curve of the transmitting function as the formula by fitting the curves, when there are information of gain and phase, to this information using the minimum square method. Usually, an FFT analyzer has such function and in actual the continuous time model is obtained with the formula using the Laplace's operator s using such function.

A model of the pseudo inverse filter (Step S8) is obtained from the continuous time model obtained here. First, when the pole obtained from the continuous time model is defined as $p_i$ (i=1 to n: order number of pole) and zero point as $z_i$, a model of the space transmitting characteristic can be obtained as indicated below using the Laplace's operator s.

$$\text{Transmitting model of } K\times Sp\times G1=K\frac{(s-z_1)(s-z_2)\cdots(s-z_n)}{(s-p_1)(s-p_2)\cdots(s-p_n)} \tag{11}$$

Here, K is a gain element. Therefore, a pseudo inverse filter to be obtained can be obtained from the inverse function where the denominator and numerator of the transmitting model are replaced with each other.

$$\text{Stable inverse filter model}=\frac{(s-p_1)(s-p_2)\cdots(s-p_n)}{K(s-z_1)(s-z_2)\cdots(s-z_n)} \tag{12}$$

Above explanation relates to the design of an inverse filter and the following explanation relates to the design of the frequency response of the transmitting portion of duct. In this design, first, the frequency response G0 up to the evaluation microphone in the silencing point from the noise source is measured (Step S9). More specifically, the sound source speaker is placed near the noise source to generate white noise. Such white noise is picked up by the evaluation microphone provided at the silencing point and this signal is detected, for example, by the FFT analyzer to measure the frequency response G0 as the space transmitting characteristic between the noise source and the silencing point. The gain characteristic obtained here is defined as g0, while the phase characteristic as p0.

Next, delay of response dt0 in the space between the sound source speaker and silencing point is obtained (Step S10). This delay of response dt0 is obtained, as the pure delay in the duct, by the following formula.

$dt0$=Distance between the sound source speaker and evaluation microphone/Sound velocity (13)

Thereby, the time delay which may be led by the duct transmitting signal processing means can be obtained. Next, the compensated phase p0H is obtained by leading the phase p0 of the frequency response G0 (Step S11). This compensated phase p0 is expressed by the following formula.

$$p0H=p0+dt0\times 360\times \text{frequency} \tag{14}$$

Example of characteristic of the frequency response G0 compensated to eliminate such time delay is shown in FIG. 5.

Figure 5A:
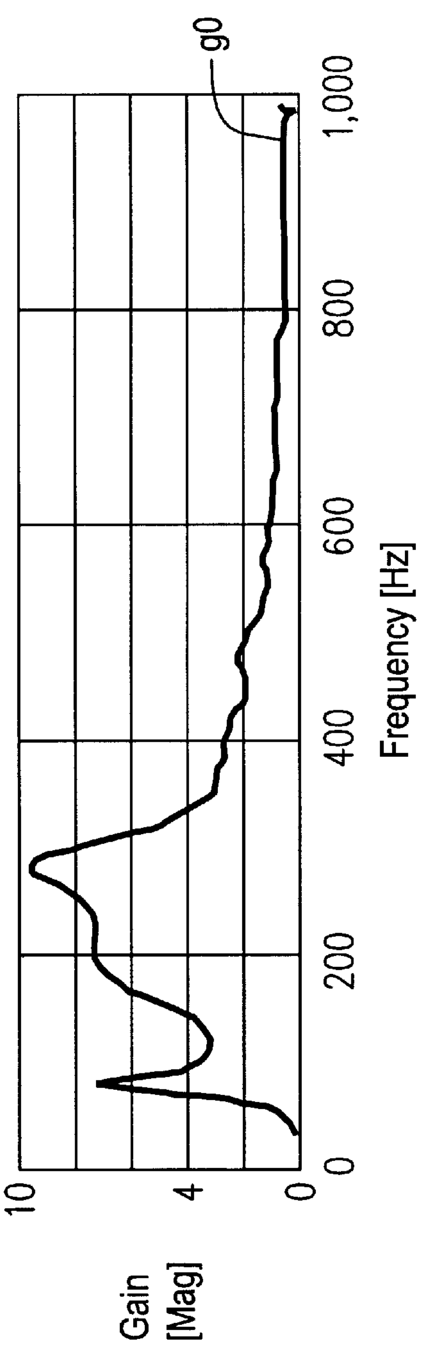
FIG. 5 shows an example of the compensated frequency response characteristic; (A) is the gain characteristic of frequency response G0 and (B) is the compensated phase characteristic.
Figure 5B:
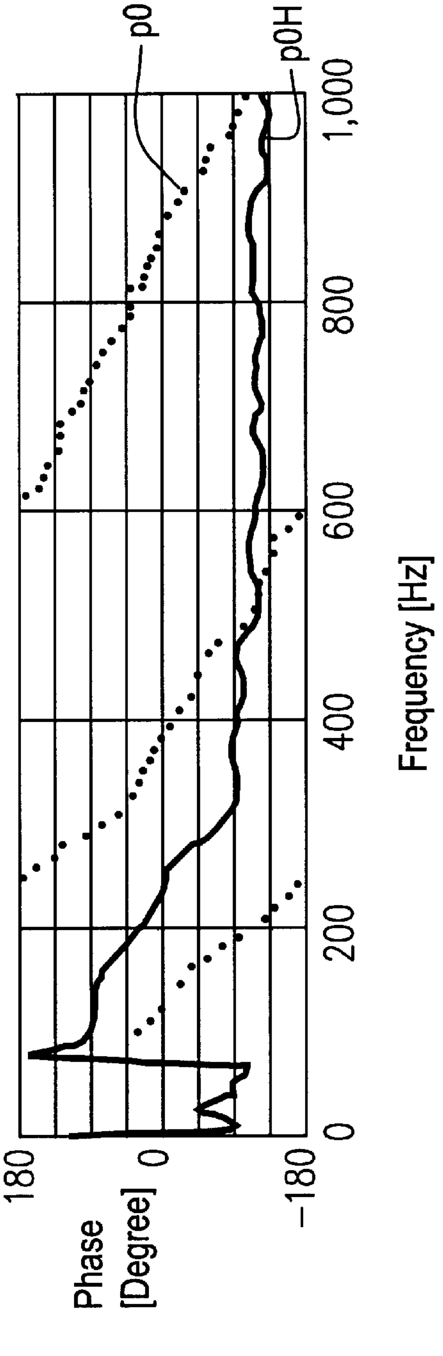

FIG. 5 is a diagram showing an example of the compensated frequency response characteristic. (A) shows the gain characteristic of the frequency response G0 and (B) shows the compensated phase characteristic. Here, the gain characteristic shown in FIG. 5(A) is the gain characteristic g0 measured in the step S9. Moreover, in the phase characteristic shown in FIG. 5(B), a broken line shows the original phase p0 measured in the step S9 while a solid line indicates the compensated phase p0H which is led to eliminate time delay depending on the formula (14).

Next, a continuous time model using the Laplace's operator s is obtained using the curve fit method from the information of the compensated G0, gain characteristic g0 and compensated phase characteristic p0H (Step S12). When the pole obtained from a such result is defined as $p_i$ (i=1 to n: Order number of pole) and the zero point as $Z_i$, this space transmitting characteristic can be modeled as indicated below.

$$\text{Transmitting model of } G0 = K \times K\,\frac{(s-z_1)(s-z_2)\cdots(s-z_n)}{(s-p_1)(s-p_2)\cdots(s-p_n)} \tag{15}$$

Here, K is the gain element.

Next, Delay 1 in the side of the combined frequency response (K×Sp×G1) is obtained (Step S13). This Delay 1 includes the amount of compensation of phase not for making unstable the inverse filter, delay due to the D/A conversion process, phase delay when the low-pass filter is provided and the time required for calculation. Therefore the sum of these delays is obtained. Namely, the theoretical value is obtained from the following formula.

Delay 1=$dt1$+$D/A$ conversion delay+phase delay of low-pass filter+calculation time (16)

Here, phase delay of low-pass filter in the formula (16) and calculation time will then be explained.

Figure 6:
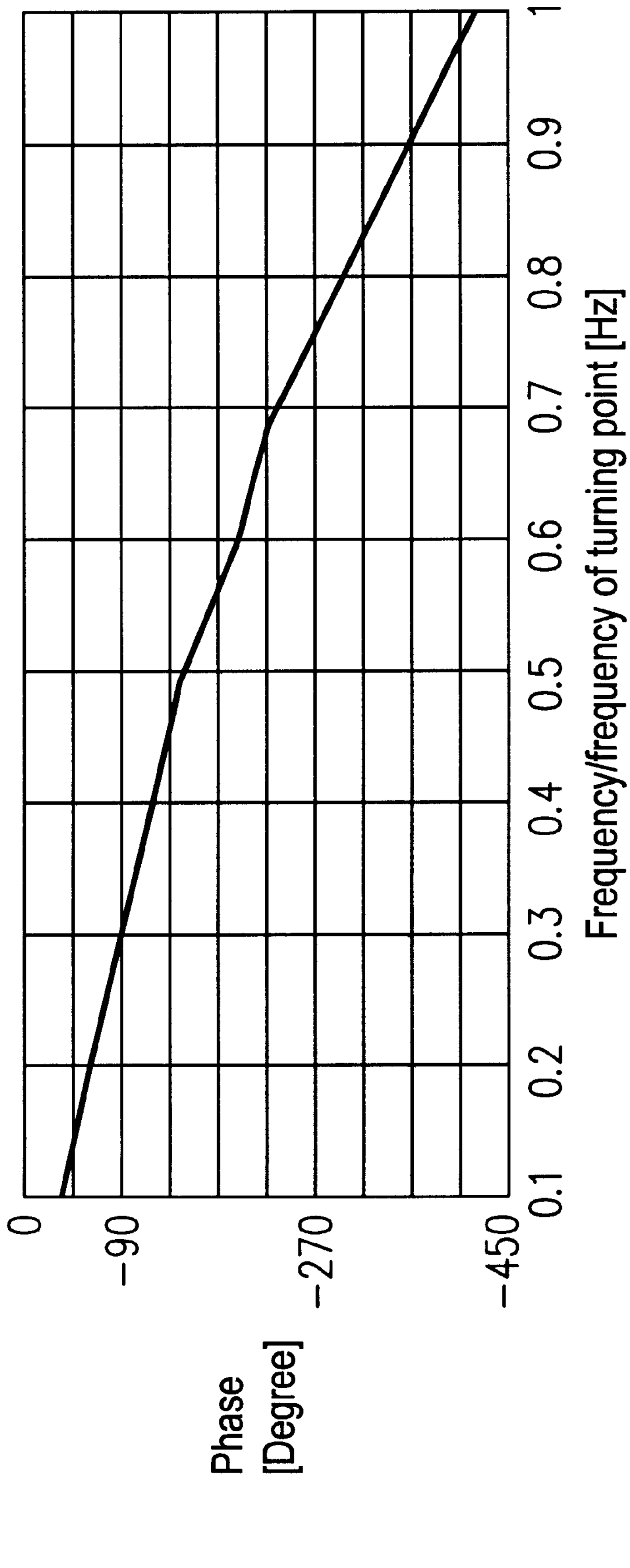
FIG. 6 shows an example of the phase characteristic of a low-pass filter.

FIG. 6 is a diagram showing an example of the phase characteristic of the low-pass filter. When the low-pass filter has the phase characteristic as shown in FIG. 6, this phase delay is converted to a time delay to define the average value as the phase delay of the low-pass filter.

Moreover, the calculation time of the formula (16) can be obtained by previously measuring the time required for filter process as the basic unit when the order number of the denominator and numerator of the transmitting model become apparent in the step S8 and step S12.

$$\text{Basic unit}=K\times(s-b)/(s-a) \tag{17}$$

In the same manner, the Delay 0 in the side of the frequency response G0 is obtained (Step S14). Since the calculation time is naturally required for the duct process, the Delay 0 in the G0 side can be obtained by the following formula.

Delay 0=$dt0$+calculation time (18)

Next, the Delay 1 and Delay 0 obtained above are compared with each other to judge whether Delay 0 is larger than Delay 1 or not (Step S15). Here, it is judged whether phase compensation is possible or not. If Delay 0 is not larger than Delay 1, phase compensation is impossible and therefore the inverse filter must be designed again. More specifically, the inverse filter is designed again from the beginning (Step S16) by lowering the value of the upper limit frequency Frq (high) of the control object frequency, or the inverse filter is re-designed (Steps S17) from the step S4 by shortening the distance between the secondary sound source speaker and the evaluation microphone or extending the distance between the sound source speaker and the evaluation microphone.

When the Delay 0 is judged to be larger than Delay 1 in the judgment of the step S15, the phase compensation is possible and therefore designing may be continued as it is. Next, the adjusting time Toff is obtained (Step S18). This adjusting time Toff may be obtained from the following formula.

Toff=Delay 0−Delay 1 (19)

Since the continuous time models of G0 and G1 may be obtained, a discrete time model for the digital process is obtained (Step S19). First, the available design information is summarized. Namely, the s model formula of the pseudo inverse filter for canceling the frequency response of K×Sp×G1, s model formula of the pseudo space transmitting characteristic of G0 and adjusting time for assuring causality may be already obtained. The operation required thereafter is discrete process of the formula of the continuous time for the digital process. When the model formula in the continuous time is already known, z conversion is known as the method of discrete process.

Various methods are prepared for z conversion, but here the matching z conversion is used. Here, it is assumed that a model expressed in the continuous time system is given by the following formula.

$$\text{Continuous time model } Cc(s) = K\,\frac{(s-q_1)\cdots(s-q_m)}{(s-p_1)\cdots(s-p_n)} \tag{20}$$

However, m, n are respectively order numbers of the numerator and denominator. In this case, the conversion formula of matching z conversion is as follow.

$$\text{Discrete time model } C(z) = K0\,\frac{(1-\mathrm{Exp}[q_1 \times dt]z^{-1})\cdots(1-\mathrm{Exp}[q_m \times dt]z^{-1})}{(1-\mathrm{Exp}[p_1 \times dt]z^{-1})\cdots(1-\mathrm{Exp}[p_n \times dt]z^{-1})} \tag{21}$$

Where, K0=C(1)/Cc(0) is defined.

The respective discrete model formulae can be derived by executing the matching z conversion depending on this conversion formula. The discrete model formula obtained in the form of formula (12) can be developed as follow.

$$\text{Discrete time model } C(z) = \frac{b_0 + b_1 z^{-1} + b_2 z^{-2} + \cdots + b_m z^{-m}}{1 + a_1 z^{-1} + a_2 z^{-2} + \cdots + a_n z^{-n}} \tag{22}$$

Relationship between this model formula and input signal data u[k] and output signal data y[k] in the discrete time can be indicated as follow.

$$y[k]=C(z)\times u[k] \tag{23}$$

However, k is a parameter indicating the current time in the discrete time. Thereby, an output y[k] at the current time k can be expressed as follow from the formulae (22) and (23).

$$Y[k]=b_0\times u[k]+b_1\times u[k-1]+b_2\times u[k-2]+ \ldots +b_n\times u[k-n]-a_1\times y[k-1]-a_2\times y[k-2]- \ldots -a_n\times y[k-n] \tag{24}$$

Namely, it can be obtained by the product and sum of the current input u[k] and input/output data in the past u[k−i] and y[k−j].

Next, the digital process of the signal processing means 25 as designed as explained above will then be explained.

Figure 7:
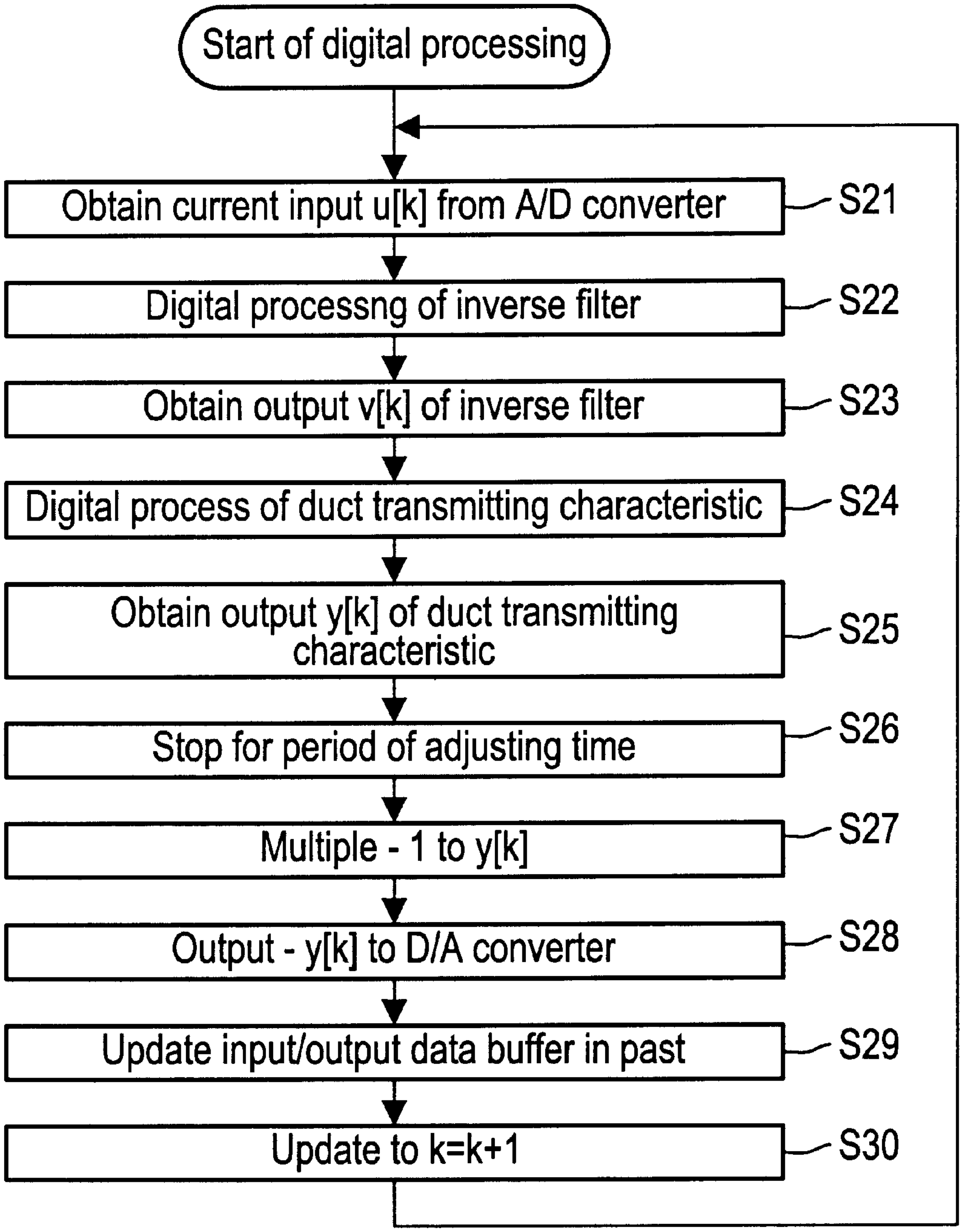
FIG. 7 is a flowchart showing the flow of digital process of the signal processing means.

FIG. 7 is a flow chart indicating the flow of the digital process of the signal processing means. First, the current input u[k] is obtained from the A/D converter 24 (Step S21). Next, the digital process of the inverse filter is executed first (Step S22). Since the discrete model formula of K×Sp×G1 is designed, the practical formula can be obtained from the formula. Next, an output v[k] of the inverse filter is obtained by the digital process (Step S23).

In the same manner, an output y[k] of G0 is obtained (Step S25) from the discrete model formula of G0 by executing the duct transmitting characteristic (Step S24).

Thereafter, the adjusting time Toff has been obtained but here the process is stopped for the period as long as the adjusting time (Step S26). After the waiting time equal to the adjusting time, −1 is multiplied to the output y[k] (Step S27), −y[k] is output to the D/A converter 28 and it is then output as the actual sound wave from the secondary sound source speaker 30 (Step S28). Here, the input/output buffer in the past is updated (Step S29). Since the current input u[k] has been processed, it is converted to one data u[k−1] in the past. Of course, the buffer is further updated by changing u[k−1] into the u[k−2] in the past. The current time is updated to k+1 from k (Step S30) and then operation is returned to the start. Repetition of such operations will complete the digital process in the signal processing means 25.

Figure 8A:
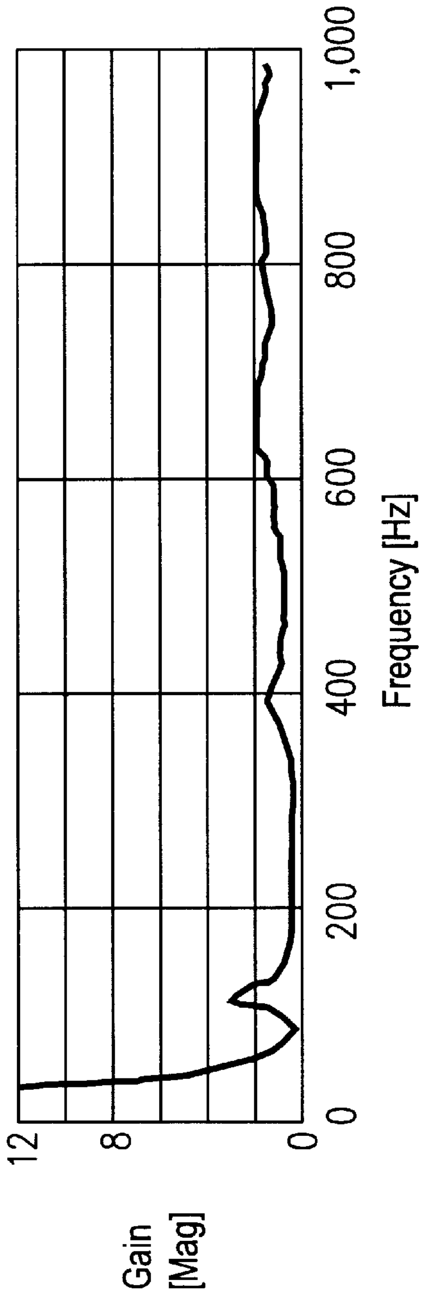
FIG. 8 shows an example of the characteristic of inverse filter signal processing means; (A) is the gain characteristic and (B) is the phase characteristic.
Figure 8B:
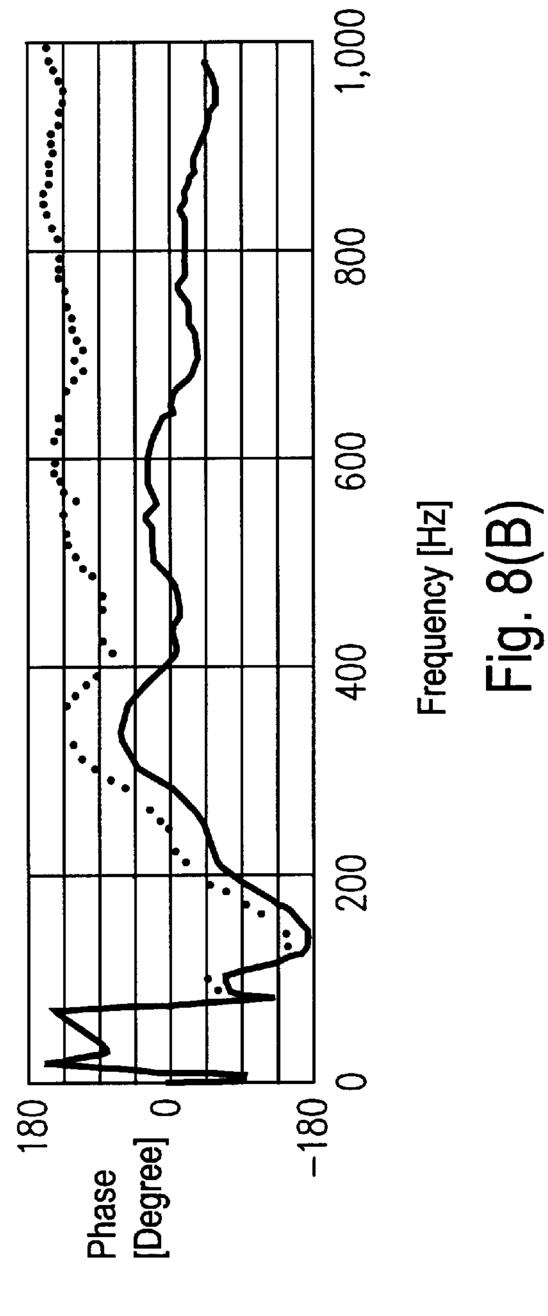

FIG. 8 is a diagram showing an example of the characteristic of the inverse filter signal processing means. (A) shows the gain characteristic, while (B) shows the phase characteristic. Here, the gain characteristic shown in FIG. 8(A) is obtained by measuring the gain characteristic which is in the relationship of the inverse number of the gain of the combined frequency response (K×Sp×G1). Moreover, in the phase characteristic shown in FIG. 8(B), a broken line indicates the phase characteristic when the phase of the combined frequency response (K×Sp×G1) is set to the relationship of the inverse filter, while a solid line indicates the minimum phase characteristic which is the only characteristic obtained for the measured gain characteristic of FIG. 8(A). As explained, when a model is formed by simply positively or negatively inverting the phase characteristic of the original combined frequency response characteristic, the phase characteristic is indicated by a broken line and thereby the model becomes unstable. Here, as indicated by a solid line in FIG. 8(B), the phase characteristic is set to show the minimum phase characteristic for the gain characteristic. Such minimum phase characteristic can be analytically obtained from the given gain characteristic by using the mathematical method such as Hilbert conversion. Appearance of unstable pole of the inverse filter signal processing means 27 can be suppressed perfectly by giving such minimum phase characteristic.

Figure 9:
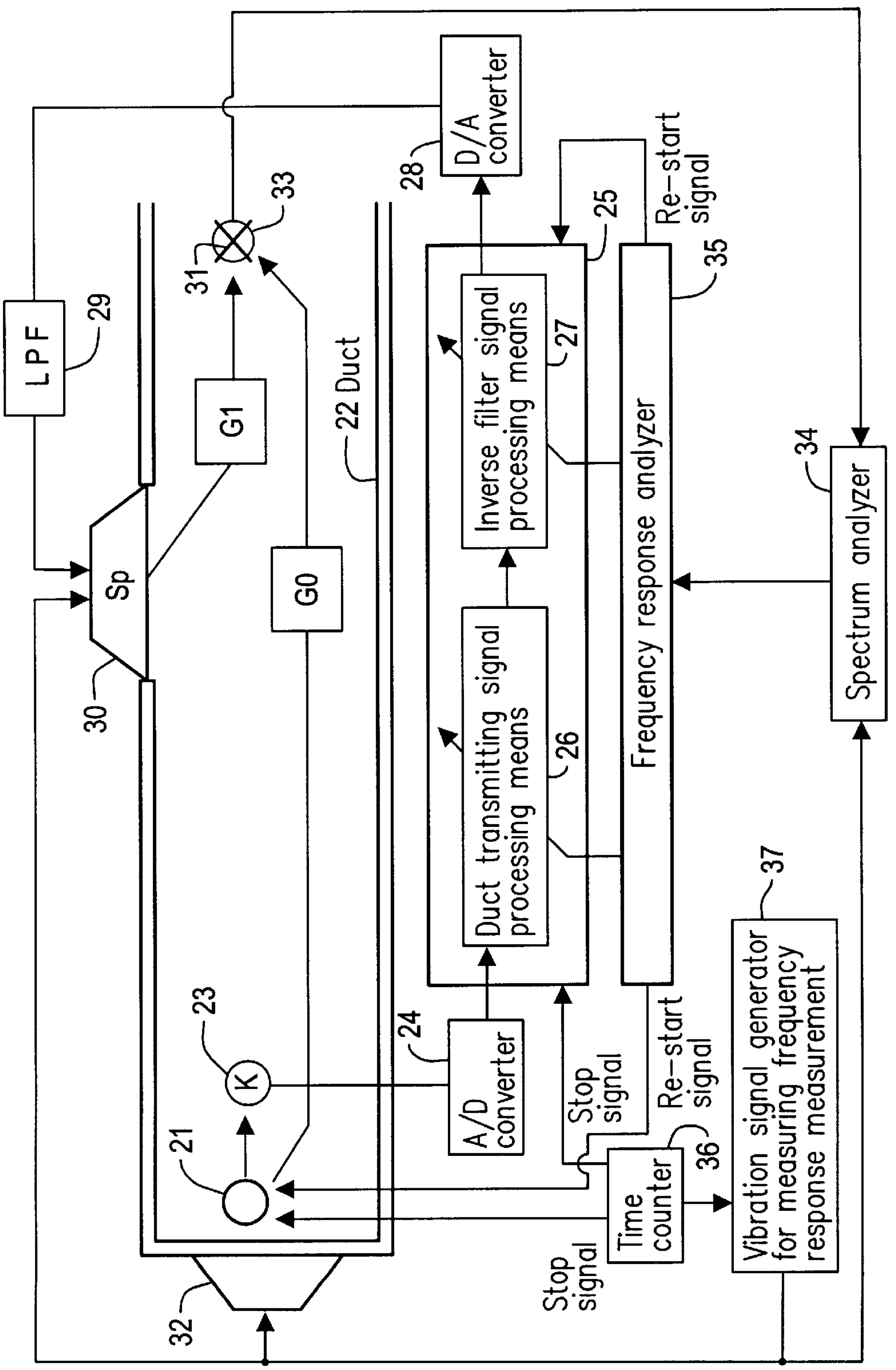
FIG. 9 is a diagram showing a second embodiment of an active silencer.

FIG. 9 is a diagram showing the second embodiment of the active silencer of the present invention. In FIG. 9, the same element as those in FIG. 2 are defined by the same reference numerals and the detail description of such element is omitted here. According to FIG. 9, there are provided, in addition to the structure of FIG. 2, a vibration signal radiating speaker 32 provided in the vicinity of the noise source 21 for radiating, the vibration signal as the sound wave, a measuring microphone 33 for measuring the radiated vibration signal at the silencing point 31, a spectrum analyzer 34 for obtaining the frequency response of each portion from the vibration signal and an output of the measuring microphone 33, a frequency response analyzer 35 for obtaining update coefficient of each digital filter within the signal processing means 25 from the result of the spectrum analyzer 34, a timer counter 36 for monitoring the update period, and a vibration signal generator 37 for measuring frequency response to generate a signal to measure the frequency response of each portion which is the design information of the signal processing means 25.

A timer counter 36 is counting the time from the preceding update of frequency response. When the predetermined time has passed, a stop signal is sent to the noise source 21 and signal processing means 25 to suspend the silencing process.

The timer counter 36 simultaneously sends a measurement start signal to the vibration signal generator 37 for measuring frequency response to start re-measurement of the frequency response. First, a vibration signal generated by the vibration signal generator 37 for measuring frequency response is given to the vibration signal radiation speaker 32 and a vibration sound is then radiated into the duct 22. The vibration sound is influenced by the space transmitting characteristic G0 and then it reaches the measuring microphone 33. In the spectrum analyzer 34, frequency response of G0 can be obtained from the vibration signal and output signal of the measuring microphone 33. The result is then sent to the frequency response analyzer 35 to determine the coefficient of the digital filter of the duct transmitting signal processing means 26. The determined coefficient is sent to the duct transmitting signal processing means 26 and the coefficient is then updated.

The similar operation is performed for the inverse filter signal processing means 27 for the combined frequency response (K×Sp×G1) up to the silencing point 31 from the input microphone 23.

When the update of coefficient of filter is all completed, a re-start signal is output from the frequency response analyzer 35 and thereby operations of the noise source 21 and signal processing means 25 are re-started to execute the silencing operation.

As explained above, G0 and (K×Sp×G1) which are data required to form the signal processing means 25 are measured in every predetermined period with a spectrum analyzer 34 and then these data are compared with the characteristic measured previously in the frequency response analyzer 35. If these data are different to a large extent, the duct transmitting signal processing means 26 and inverse filter signal processing means 27 are re-designed to update the coefficient according to the algorithm of the design flow chart of FIG. 3 in order to re-start the silencing operation. Accordingly, if environmental change such as deterioration of parts is generated, the fixed coefficient of digital filter is updated in every predetermined period during the silencing operation and thereby the silencing effect can be maintained for a long period of time.

Figure 10:
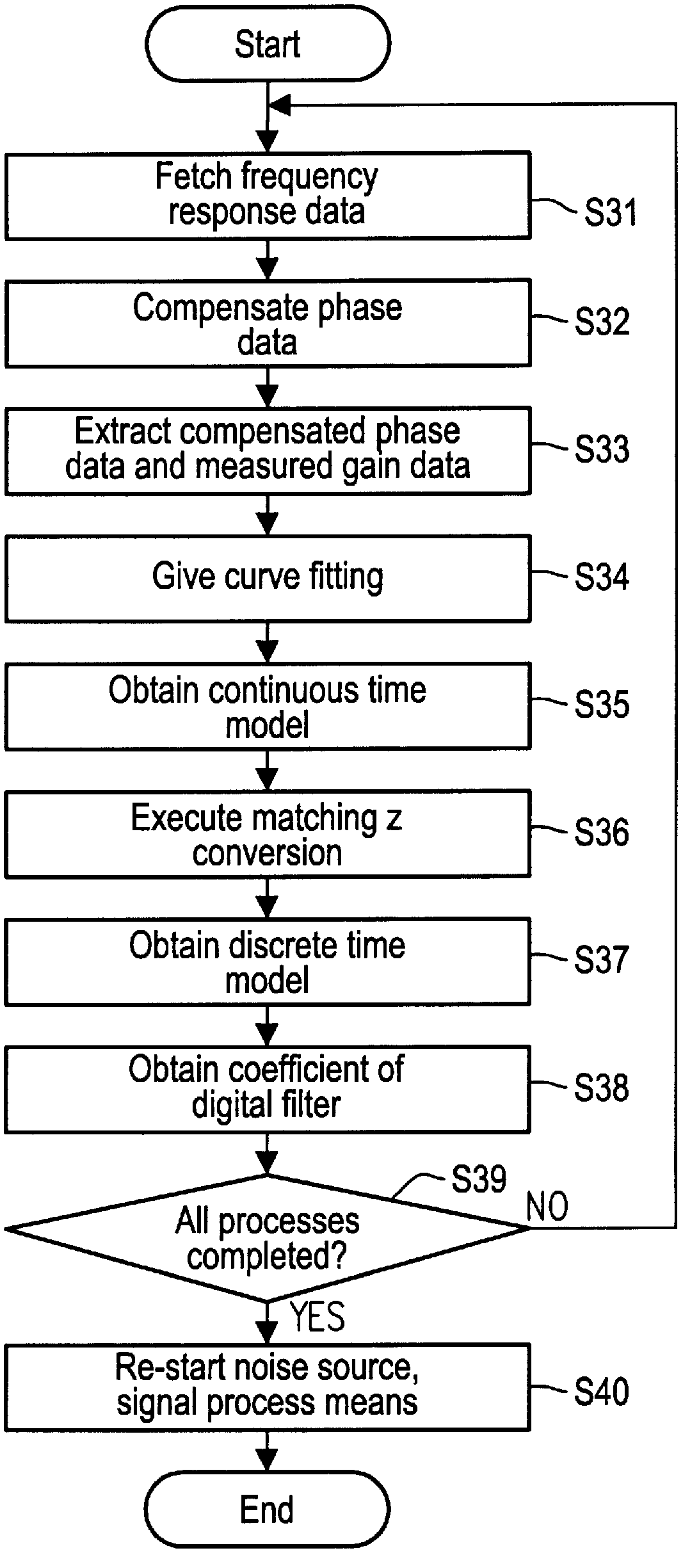
FIG. 10 is a flow chart showing the flow of process of a frequency response analyzer.

FIG. 10 is a flow chart showing the flow of process of the frequency response analyzer. Here, the process for actually re-designing the frequency response analyzer 35 by receiving the measuring result of the spectrum analyzer 34 will be explained. First, the frequency response data measured again by the spectrum analyzer 34 is fetched (Step S31). Next, the data of measured phase characteristic is compensated (Step S32). Here, the phase data is compensated based on the information of the phase compensation amount which is already obtained at the time of design.

Next, the compensated phase data and measured gain data are extracted (Step S33) and a curve fitting is made to these data using the minimum square method, etc. (Step S34) in order to obtain a continuous time model (Step S35). Next, the matching z conversion is executed (Step S36) for the continuous time model on the basis of the information of sampling period obtained from the control frequency which is determined at the time of design. With this matching z conversion, the discrete time model is determined (Step S37) and update is executed (Step S38) by obtaining the coefficient of the digital filter from the discrete time model. Here, this coefficient is compared with the preceding coefficient of the digital filter. If there is no large difference as a result of comparison, it is possible not to perform the update. Next, whether processes of all digital filters are completed or not is judged (Step S39). Here, if update of all digital filters is not yet completed, operation returns to the step S31. When it is confirmed that update of all digital filters is completed, the re-start signal is sent to the noise source and signal processing means to re-start the silencing operation (Step S40).

Figure 11:
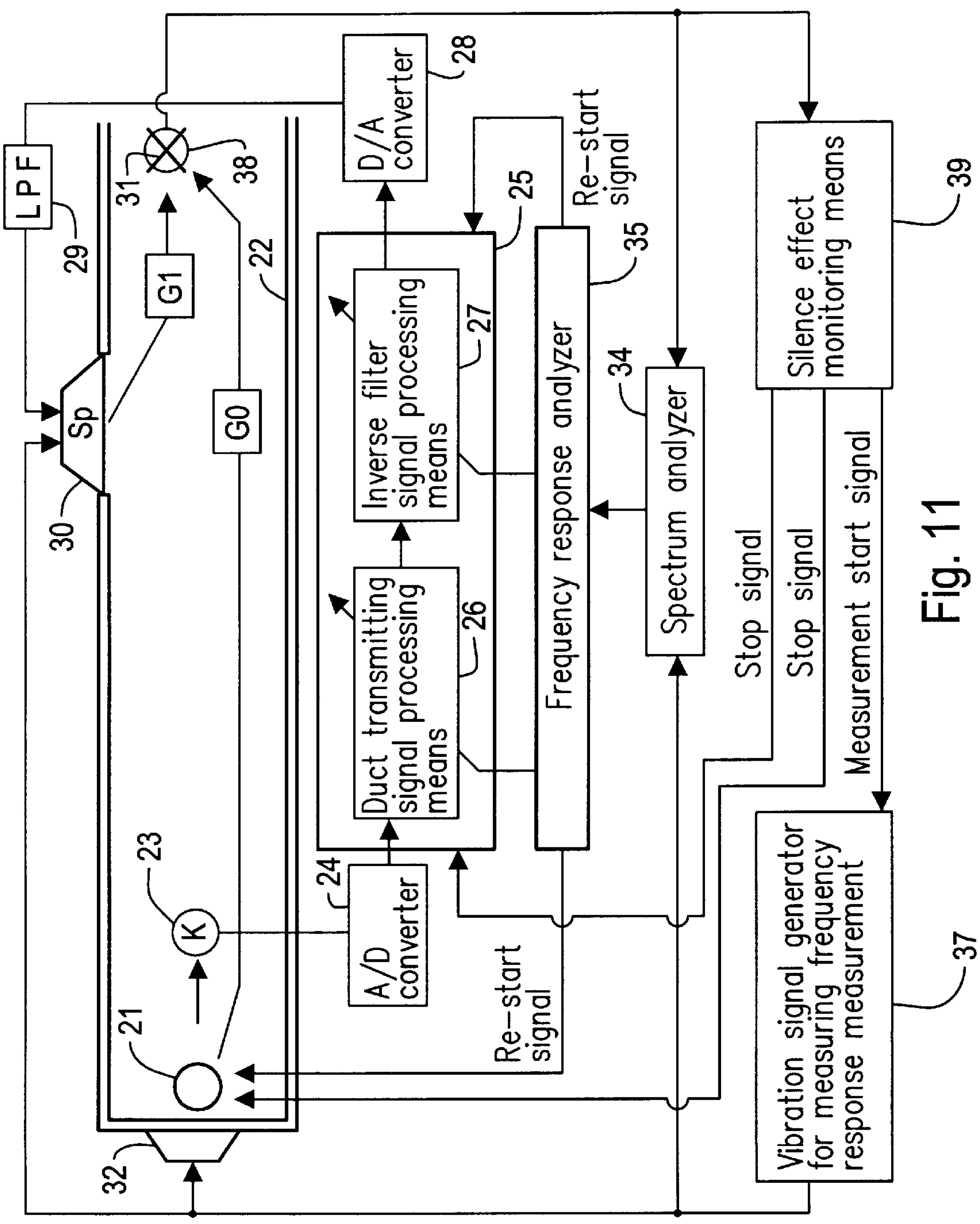
FIG. 11 is a diagram showing the third embodiment of an active silencer.

FIG. 11 is a diagram showing the third embodiment of the active silencer. In FIG. 11, the elements like those in FIG. 2 and FIG. 9 are designated by the like reference numerals and detail description of these elements is omitted. According to FIG. 11, there are provided silencing effect monitoring means 39 for inputting an output signal of a silence detecting microphone 38 to detect sound pressure at the silencing point 31, in addition to the vibration signal radiating speaker 32 for re-designing the signal processing means 25, a silence detection microphone 38, a spectrum analyzer 34, a frequency response analyzer 35, and a vibration signal generator 37 for measuring frequency response.

The secondary sound for silencing from the secondary sound source speaker 30 and noise from the noise source 21 are interfered with each other and the noise of which sound pressure is reduced is detected by the silence detecting microphone 38 provided at the silencing point 31. The result is sent to the silence effect monitoring means 39 and is then compared with the predetermined allowable value.

Therefore, if amount of noise, after reduction thereof, exceeds the allowable value, the silence effect monitoring means 39 sends a stop signal to the noise source 21 and signal processing means 25 to stop the silencing operation. The same silence effect monitoring means 39 sends a measurement start signal to the vibration signal generator 37 for frequency response measurement to re-start the measurement of frequency response. First, the vibration signal generated by the vibration signal generator 37 for frequency response measurement is supplied to the vibration signal radiating speaker 32 provided in the vicinity of the noise source and a vibration sound is radiated therefrom into the duct 22. After receiving influence of the space transmitting characteristic G0, the vibration sound reaches the silence detecting microphone 38. The vibration signal and an output signal of the silence detecting microphone 38 are input to the spectrum analyzer 34 and the frequency response of G0 is obtained from these signals. The result is then sent to the frequency response analyzer 35 to determine the coefficient of the digital filter of the duct transmitting signal processing means 26. The determined coefficient is sent to the duct transmitting signal processing means 26 to update the coefficient.

The similar operation is also performed for the inverse filter signal processing means 27 for the combined frequency response up to the silencing point 31 from the input microphone 23.

When updating of coefficient of the filter is all completed, the frequency response analyzer 35 sends the re-start signal to the noise source 21 and signal processing means 25. Thereby, the silencing operation is started again. The flow of process of the frequency response analyzer 35 is same as the flow of process in FIG. 10.

As explained above, the silence effect at the silencing point 31 is monitored on the real time basis and when the silence effect monitoring means 39 has judged the silence effect is lowered, the silence process is stopped, the signal processing means 25 is re-designed and the coefficient of the digital filter of the signal processing means 25 is updated to start again the silence process. Therefore, if environment changes, the silence effect may be maintained corresponding to such environmental changes.

FIG. 12 is a diagram showing the fourth embodiment of the active silencer of the present invention. (A) shows a structure when the filter coefficient is assumed, while (B) shows a structure when silence process is executed. In FIG. 12, the elements like those of FIG. 2 and FIG. 9 are designated by the like reference numerals and the detail description is not repeated here. According to FIG. 12, when the coefficient of the digital filter is estimated, a white noise generator 40 for estimation generates white noise for estimation from the area near the noise source 21, the signal processing means 25 respectively receives the white noise signal x(t) for estimation from the detection microphone 23*a* provided near the noise source 21 and an error signal e(k) from the error detection microphone 41 provided at the silencing point 31 to operate as an application filter and gives the processed signal to the secondary sound source speaker 30. Moreover, during the silence process, the signal processing means 25 functions as a fixed filter to give the signal obtained by processing the noise signal received from the input microphone 23*a* to the secondary sound source speaker 30.

Figure 12A:
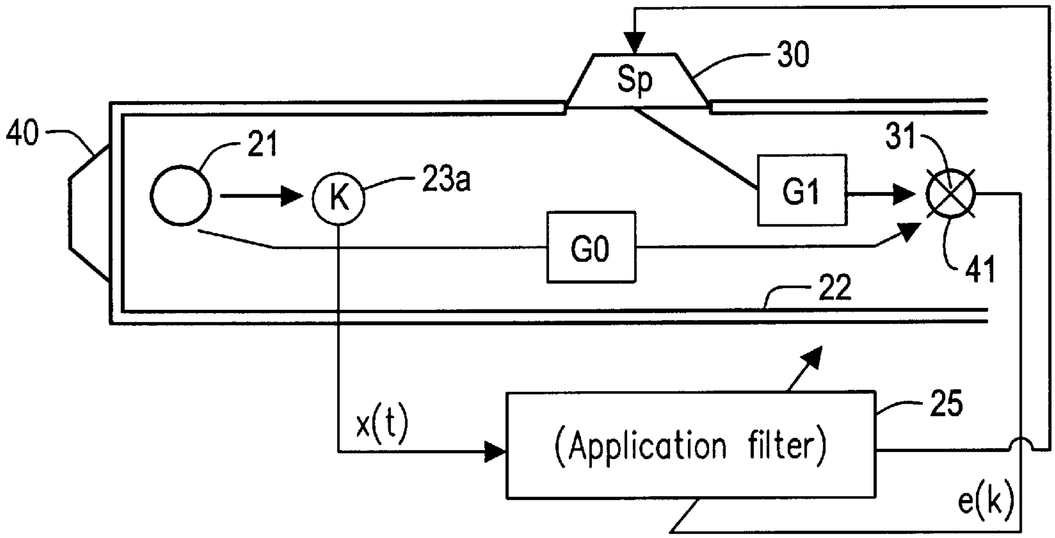
FIG. 12 shows a fourth embodiment of the fourth embodiment of an active silencer; (A) is the structure for estimating the filter coefficient and (B) is the structure for silence process.

First, in the structure of FIG. 12(A), the white noise signal generator 40 for estimation provided in the vicinity of the noise source 21 radiates white noise having the frequency element of the frequency band to be silenced under the condition that noise generation from the noise source 21 is interrupted. Such noise is detected by the detection microphone 23*a* and the signal processing means 25 estimates the filter coefficient of the application filter which makes zero the sound pressure at the silencing point 31 using the application filter system from the noise signal x(t) and the error signal e(k) detected by the error detection microphone 41 provided at the silencing point 31 in the duct 22. When the updated amount of the filter coefficient is lower than the preset threshold value as a result of estimation, the white noise signal generator 40 for estimation is stopped to complete the estimation of the filter coefficient.

Figure 12B:
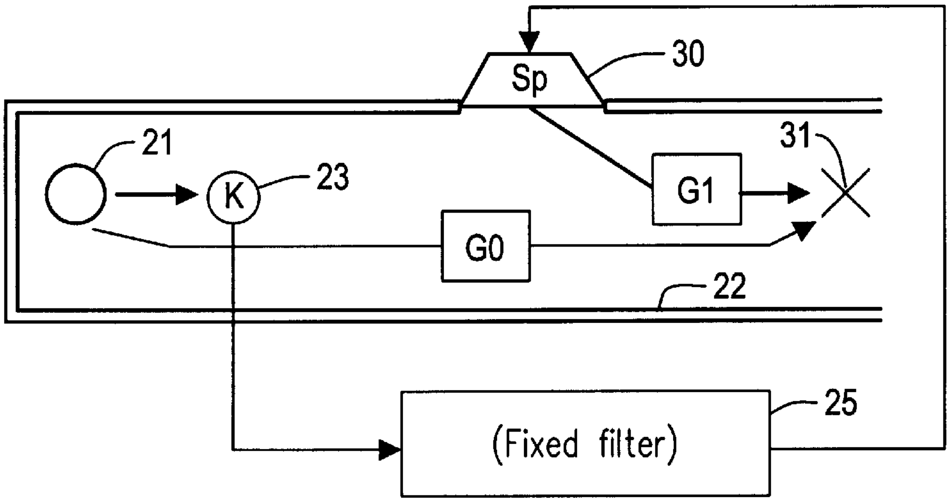

Like the structure of FIG. 12(B), the signal processing means 25 fixes the coefficient of the application filter obtained as a result of estimation of filter coefficient to form a fixed filter of the fixed parameter system. When the silence process is executed, generation of noise is started again from the noise source 21 and the noise signal obtained from the input microphone 23 is processed by the signal processing means 25 to radiate the processing result to the duct 22 from the secondary sound source speaker 30. Thereby, the noise and secondary sound are interfered at the silencing point 31 and these sounds are canceled with each other to realize silencing.

Figure 13:
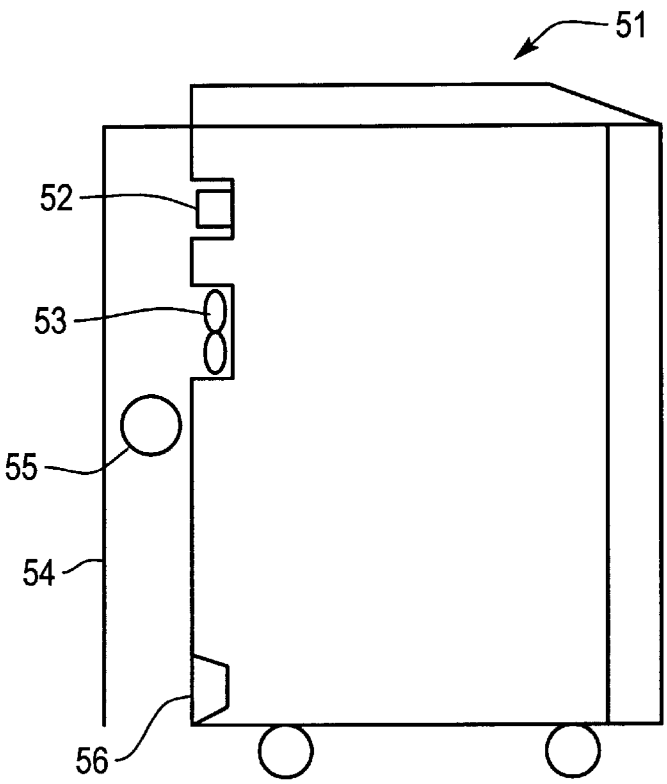
FIG. 13 is a diagram showing an application example into a copying machine of an active silencer.

FIG. 13 is a diagram showing application example of the active silencer into a copying machine. A copying machine 51 is provided with a driving apparatus 52 and a heat radiating fan 53 at its rear portion. In this case, these driving apparatus 52 and heat radiating fan 52 are noise sources of the copying machine 51. In this copying machine 51, a rear surface duct 54 is provided to surround the driving apparatus 52 and heat radiating fan 63 and is provided with an aperture at the bottom portion thereof. Within this rear surface duct 54, an input microphone 55 is provided in the downstream side of the noise source and a secondary sound source speaker 56 which radiates the secondary sound is also provided at the area near the aperture of the rear surface duct 54.

In this structure, noise generated from the driving apparatus 52 and heat radiating fan 53 is detected by the input microphone 55 and is then input to signal processing means not illustrated. The signal processing means generates the signal having the same amplitude and inverse phase from the noise waveform detected by the input microphone 55 and is also manipulated in its amount of phase and this signal is then radiated to the duct aperture through the secondary sound source speaker 56. Thereby, the noise radiated from the driving apparatus 52 and the heat radiating fan 53 and the secondary sound radiated from the secondary sound source speaker 56 are interfered with each other at the duct aperture to reduce the sound level of the noise.

Figure 14:
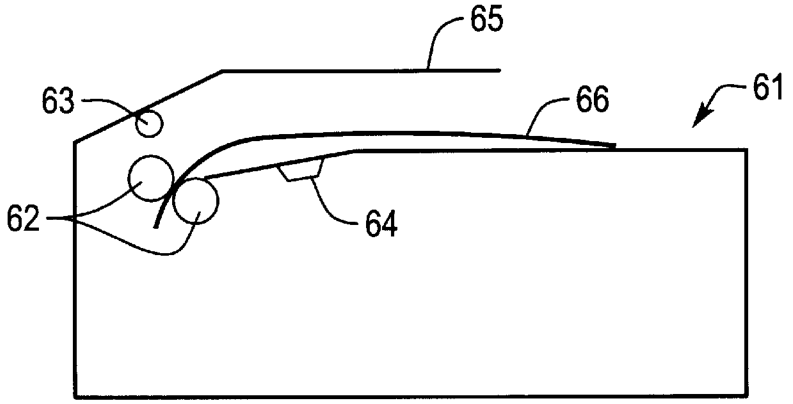
FIG. 14 is a diagram showing an application example into a laser printer of an active silencer.
Figure 15:
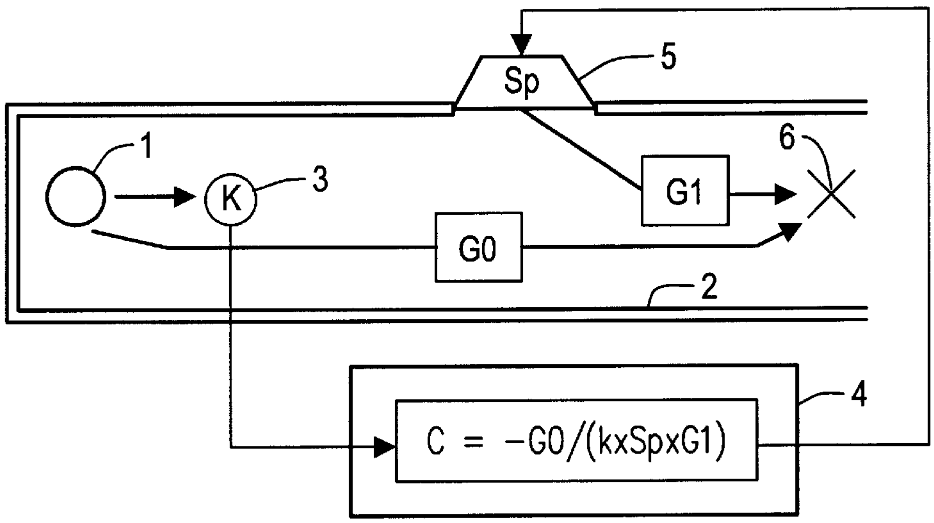
Fig. 15 Prior Art
FIG. 15 is a diagram showing an example of the basic structure of the silencer of the related art.
Figure 16:
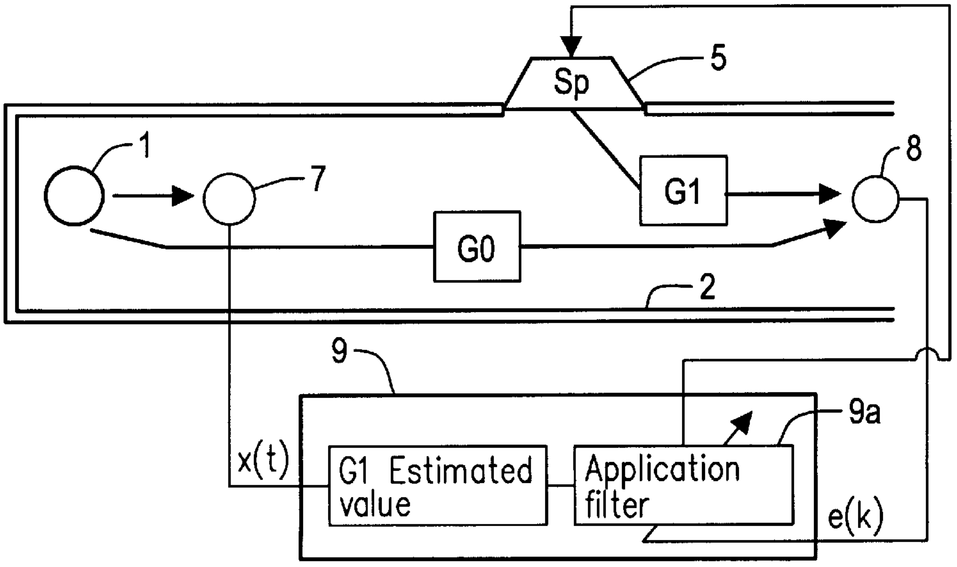
Fig. 16 Prior Art
FIG. 16 is a diagram showing an example of another basic structure of the silencer of the related art.

FIG. 14 is a diagram showing an application example of the active silencer of the present invention into a laser printer. In the laser printer 61, a paper feed roller 62 is provided at its paper exhaust port and an input microphone 63 is provided at the area near the paper feed roller 62. Moreover, the body in the exist side of the paper exhaust port is provided with the secondary sound source speaker 64. This paper exhaust port is provided with a duct cover 65 as the covering means. Here, in the paper exhaust port of the laser printer 61, a noise similar to white noise is generated due to the friction of paper feed roller 62, paper feeding part and a paper 66 and these portions are forming a noise source.

In such a structure, paper exhausting noise generated when the paper 66 is fed is detected by an input microphone 63 and is then input to signal processing means not illustrated. The signal processing means generates the signal in the same amplitude and inverse phase from the waveform of the paper exhausting noise detected by the input microphone 63 and then gives this signal to the secondary sound source speaker 64. Thereby, the signal in the same amplitude and inverse phase from the waveform of the paper exhausting noise and manipulated as much as the phase amount is radiated into the duct formed by the duct cover 65 from the secondary sound source speaker 64 and this signal is interfered with by the paper exhausting noise generated from the paper feed roller 62 and paper feeding parts to reduce the sound level of the paper feeding noise.

In above embodiments, a microphone which detects sound wave in the air is used as a means for obtaining a noise signal from the noise source, but it is also possible to use, in place of the microphone, a sensor for measuring acceleration of vibration of the noise source (compressor, motor, etc.) which is generating noise.

As explained above, the present invention has divided the signal processing means which has been designed as one unit is divided to the part of the inverse filter process which results in a cause of instability and the part of the stable space transmitting process. Since the cause of instability in the inverse filter process lies in the execution of the process while delay of response is included, the pseudo inverse filter processing means is formed by eliminating such delay and meanwhile such delay is compensated by the space transmitting processing part. Thereby, the signal processing means as a whole can be stabilized. Moreover, since the application calculation including a large amount of calculation is not executed, the calculation time can be reduced remarkably and the distance which has been required to a certain extent between the input microphone and the secondary sound source speaker to assure the calculation time can be reduced now. Accordingly, reduction in size of apparatus can be realized. Therefore, noise can be silenced with a small size and low cost system without using an exclusive high speed calculation element. In this viewpoint, the present invention can be applied into the apparatus such as a small size home electronic device and OA apparatus which cannot introduce the active silencer because of the limitation on the size and cost.

Since the silence control is performed by the open loop, stability of the control system as a whole can also be assured and the control system will never generate uncontrolled operation even if sudden noise from the external side of control system and noise other than the silencing object is generated.

Moreover, since stability of signal processing filter is assured by manipulation of the phase amount within the signal processing means, it is not required to employ the FIR filter structure which assures stability but requires a longer time and IIR filter structure which does not require the longer time can be introduced. Thereby, remarkable shortening of the calculation time can be estimated.

In addition, for the environmental change in the surrounding of the apparatus, the frequency response of each part is measured again based on the frequency response design of the signal processing means and the frequency response of the signal processing means can be structured again based on the result of above measurement.

Moreover, the similar effect can also be obtained by executing the application arithmetic operation which requires a longer time in separation from the silence control and then fixing the frequency response characteristic of the signal processing means in the silence control to the time.

What is claimed is:

1. An active silencer comprising noise input means for obtaining a noise signal from noise generated by a noise source, signal processing means for converting the noise signal obtained by said noise input means into the signal waveform having the same amplitude as that of the noise waveform and inverse phase thereto propagated from said noise source, and a secondary sound source speaker for radiating the signal converted by said signal processing means as the sound wave in order to cause the noise from the noise source and the sound wave radiated from said secondary sound source speaker to be interfered with each other at a preset silencing point, wherein said signal processing means further comprising:

pseudo space transmitting signal processing means for converting the noise signal obtained by said noise input means into the signal having the same amplitude characteristic as the frequency response characteristic of the sound wave up to said silencing point from said noise source and the phase characteristic delayed by a first predetermined amount (td−tp) for said frequency response characteristic; and pseudo inverse filter signal processing means for converting the signal converted by said pseudo space transmitting signal processing means into the signal having the amplitude characteristic which is the inverse of the frequency response characteristic of the sound wave up to the silencing point through said noise input means, said secondary sound source speaker, and the space from said secondary sound source speaker to said silencing point and also having the phase characteristic delayed by a second predetermined amount (tp) from the positively or negatively inverted phase for the frequency response characteristic of the sound wave.

2. An active silencer according to claim 1, wherein the phase characteristic of said pseudo inverse filter signal processing means in a copying machine is the minimum phase transition system for the gain characteristic of said signal processing means.

3. An active silencer according to claim 2, wherein said silencing point is set far from the position of said secondary sound source speaker when said input means is defined as the base point; the predetermined amount for leading the phase characteristic in the pseudo space transmitting signal processing means is equal to the time for delaying the phase characteristic in the pseudo inverse filter signal processing means; and the second predetermined amount for delaying the phase characteristic in said pseudo inverse filter signal processing means is determined depending on a phase difference between the minimum phase of the frequency response characteristic up to said silencing point through said noise input means, said secondary sound source speaker and the space up to said silencing point from said secondary sound source speaker and the actual phase.

4. An active silencer according to claim 2, wherein said silencing point is set far from the position of said secondary sound source speaker when said noise input means is defined as the base point;

the first predetermined amount for leading the phase characteristic in said pseudo space transmitting signal processing means is determined depending on a phase difference between the minimum phase of the frequency response characteristic of the sound wave up to said silencing point from said noise source and the actual phase; and the second predetermined amount for delaying the phase characteristic in said pseudo inverse filter signal processing means is determined depending on a phase difference between the minimum phase of the frequency response characteristic up to said silencing point through said noise input means, said secondary sound source speaker and the space from said secondary sound source speaker to said silencing point and the actual phase.

5. An active silencer according to claim 2, comprising:

measuring means for measuring frequency response up to said silencing point from said noise source, frequency response of said noise input means, frequency response of said secondary sound source speaker, and frequency response up to said silencing point from the secondary sound source speaker; and retrial setting means for updating in every predetermined time the frequency response of said pseudo space transmitting signal processing means and said pseudo inverse filter signal processing means depending on result of measurement by said measuring means.

6. An active silencer according to claim 2, comprising:

silence detecting means for detecting the combined sound at said silencing point of the noise from the noise source and the sound wave from said secondary sound source speaker;

silence effect monitoring means for comparing the combined sound detected by said silence detecting means with a preset allowable value;

measuring means for measuring, when the combined sound compared by said silence effect monitoring means has exceeded the allowable value, the frequency response up to said silence point from said noise source, frequency response of said noise detecting means, frequency response of said secondary sound source speaker, and frequency response up to said silence point from said secondary sound source speaker; and updating means for updating the frequency response characteristics of said pseudo space transmitting signal processing means and said pseudo inverse filter signal processing means depending on the result of measurement by said measuring means.

7. An active silencer according to claim 1, wherein said signal processing means is capable of fixing the input/output transmitting characteristic based on an estimation of filter coefficients during silence control operation.

* * * * *